United States Patent [19]
Jackson

[11] Patent Number: 5,312,251
[45] Date of Patent: May 17, 1994

[54] DENTAL IMPLEMENT

[76] Inventor: Paul C. Jackson, 1903 Knollton Rd., Lutherville, Md. 21093

[21] Appl. No.: 77,741

[22] Filed: Jun. 18, 1993

[51] Int. Cl.$^5$ .............................................. A61C 3/02
[52] U.S. Cl. ......................................... 433/88; 51/436
[58] Field of Search ..................... 433/88; 51/427, 436

[56] References Cited

U.S. PATENT DOCUMENTS

| | | | |
|---|---|---|---|
| 2,612,732 | 10/1952 | Ziegler | 51/436 |
| 2,759,266 | 8/1956 | Cassani | 433/88 |
| 3,067,765 | 12/1962 | Aymar et al. | 137/376 |
| 3,163,963 | 1/1965 | Caron | 51/11 |
| 3,618,263 | 11/1971 | Weijsenburg | 51/8 |
| 3,626,841 | 12/1971 | Schachter | 51/8 |
| 3,759,483 | 9/1973 | Baxter | 251/5 |
| 3,882,638 | 5/1975 | Black | 51/12 |
| 3,972,123 | 8/1976 | Black | 433/88 |
| 4,090,334 | 5/1978 | Kurowski et al. | 51/436 |
| 4,174,571 | 11/1979 | Gallant | 433/88 |
| 4,214,871 | 7/1980 | Arnold | 433/88 |
| 4,487,582 | 12/1984 | Warrin | 433/88 |
| 4,635,897 | 1/1987 | Gallant | 251/5 |
| 4,708,534 | 11/1987 | Gallant | 406/75 |
| 4,733,503 | 3/1988 | Gallant et al. | 51/410 |
| 4,893,440 | 1/1990 | Gallant et al. | 51/436 |
| 4,941,298 | 7/1990 | Fernwood et al. | 51/438 |
| 5,088,924 | 2/1992 | Woodward | 433/126 |
| 5,096,418 | 3/1992 | Loss | 433/29 |

FOREIGN PATENT DOCUMENTS 2314294  3/1972  Fed. Rep. of Germany .

OTHER PUBLICATIONS

American Dental Laser KCP 2000 brochure.

*Primary Examiner*—John J. Wilson
*Attorney, Agent, or Firm*—Richard C. Litman

[57] ABSTRACT

A dental implement is disclosed that uses a conventional tank of pressurized medical grade nitrogen, a flow control box downstream from it that receives input from a standard dentist's handpiece airflow control, a mixing chamber that holds the abrasive and includes a secondary nitrogen flow line that will "fluff up" the abrasive when sufficient gas flow is allowed to pass through it, thus entraining the abrasive within the nitrogen flow, and a handpiece that has a directing nozzle for application of the flow on a specific worksite with a fiber optic bundle having a replaceable, resilient light transmissive tip to direct light on the worksite.

11 Claims, 5 Drawing Sheets

DENTAL IMPLEMENT

BACKGROUND OF THE INVENTION

1. Field of the Invention

The present invention relates to dental implements. More specifically, it relates to a dental implement that uses pressurized medical grade nitrogen to impel granules of aluminum oxide entrained in the nitrogen flow for use in preparing a tooth for receiving a filling or composite restoration.

2. Description of the Prior Art

A new trend in dentistry is to replace the conventional, well known drill with a high velocity stream of gas having entrained particles within it. This allows for removal of the decayed area or old filling in or on the tooth's surface without heat or shock, and in many cases, without the use of anesthetics. Additionally, the surface is roughened during the process, which promotes better bonding with the composite material. One of the drawbacks of other intraoral air abrasive devices is their prohibitive cost. With the overhead burden on dentists already being extraordinarily high, this precludes many practitioners from obtaining them.

There have been a great many patents issued that relate to the present invention, and they will be discussed hereinafter, grouped according to the general thrust of their subject material.

The first group are the patents that deal specifically with entrained particles in a stream having a dental application.

In U.S. Pat. No. 3,626,841, issued on Dec. 14, 1971 to Zvi Harry Schachter there is disclosed an abrasive propellant apparatus. The mixing chamber of the device has a length of tubing having a threaded end. There is a cap having a flowable material inlet orifice at the base of the tube proximate the flexible conduit that connects the nozzle to the mixing chamber. This is an extraoral device that would be used for lab work. U.S. Pat. No. 4,941,298 issued on Jul. 17, 1990 to Mark Fernwood et al. discloses a rear reservoir micro sandblaster. In this invention, the body of the device has a pulverant material supply tube and a compressed air supply line. The compressed air supply tube is compressed by a pinch lever and, if this lever is depressed to allow the air to flow, a vacuum is created in the vortex chamber proximate the nozzle, which draws the pulverant material from the reservoir to the vortex chamber to mix with the gas, and thus be propelled out the nozzle. In contradistinction to the present invention, the Fernwood et al. device is primarily an extraoral device that, when used intraorally, is utilized for the repair of fixed prosthetics.

In U.S. Pat. Nos. 3,972,123 and 3,882,638 issued, respectively, on Aug. 3, 1976 and May 13, 1975, both to Robert B. Black there is disclosed air-abrasive prophylaxis equipment. Centrally disposed within the abrasive mixing device is a receptacle to receive the gasses, containing ports to mix the abrasive and the air as it is passed through. The abrasive laden gas is then directed through a controlling pinch valve to the hand piece.

Next is U.S. Pat. No. 4,174,571 issued on Nov. 20, 1979 to Ben J. Gallant. In this document, a method for cleaning teeth using water soluble abrasive particles is disclosed.

In U.S. Pat. No. 4,214,871 issued on Jul. 29, 1980 to Carter H. Arnold, there is disclosed a method and apparatus for cleaning teeth. The method disclosed involves water soluble halite pellets entrained within a liquid stream.

In U.S. Pat. No. 4,487,582 issued on Dec. 11, 1984 to George E. Warrin there is disclosed a dental cleaning system wherein a stream of soluble abrasive powder entrained in a stream of air is surrounded by a water spray curtain and directed at the surface of a tooth to clean the same.

The second group of patents are related to entrained abrasives in an air flow. These patents are listed below but will not be discussed in detail.

| PAT. NO. | INVENTOR | DATE OF ISSUE |
| --- | --- | --- |
| 3,163,963 | Racine Caron | January 5, 1965 |
| 3,618,263 | Per Torsten Weijsenburg | November 9, 1971 |
| 4,090,334 | Benedict Kurowski | May 23, 1978 |
| 4,708,534 | Ben J. Gallant | November 24, 1987 |
| 4,733,503 | Ben J. Gallant et al. | March 29, 1988 |
| 4,893,440 | Ben J. Gallant et al. | June 16, 1990 |
| DE 2314294 | Robert B. Black | October 18, 1973 |

The next group of patents relate to tubal flow shutoff mechanisms. First is U.S. Pat. No. 3,759,483 issued to Thomas D. Baxter on Sep. 18, 1973. This control valve has a pair of ports that drive a piston connected to a cam member. When the piston travels, the attached camming member drives one of the two valve closure members towards the other, crimping the flexible conduit that lies between them.

Another tube flow shutoff device is seen in U.S. Pat. No. 4,635,897 issued on Jan. 13, 1987 to Ben J. Gallant. In this patent, a plunger cuts off the flow in the tube. The plunger is driven by a cylinder and piston arrangement that, in turn, is driven by compressed air or the like.

Another group of patents relevant to the present invention are those dealing with fiber optics associated with dental handpieces. First of these is U.S. Pat. No. 5,088,924 issued on Feb. 18, 1992 to Gary Woodward. This discloses a dental headpiece hose that with a plurality of inner components to provide drive air, an exhaust line, chip air, and coolant water. The hose also contains a fiber optic bundle for lighting the working area.

The other patent in this group is U.S. Pat. No. 5,096,418 issued on Mar. 17, 1992 to Ronald G. Coss. The device has a special channel within it to carry a fiber optic bundle for lighting the work area.

U.S. Pat. No. 3,067,765 issued on Dec. 11, 1962 to Robert H. Aymer et al. discloses a foot control for dental accessories.

And lastly, an American Dental Laser (ADL) brochure delineating the advantages of this type of device is enclosed. Unlike the present invention, the ADL device utilizes compressed air from the dentist's existing supply and further compresses this air to achieve a cutting level.

The present invention allows the practitioner to simply detach the standard air driven drill from the existing airflow control means and plug the air transport hose, with its conventional four hole connector, into the control unit of the instant invention for nitrogen flow control purposes. The present invention also allows for more inexpensive construction in that the pressures being generated at points along the gas flow and abrasive entraining route never exceed 170 PSI.

None of the above inventions and patents, taken either singly or in combination, is seen to describe the instant invention as claimed.

SUMMARY OF THE INVENTION

The present invention is a dental implement that uses a conventional tank of pressurized medical grade nitrogen, a flow control box downstream from it that receives input from a standard dentist's handpiece control, a fluid tight mixing chamber that holds the abrasive and includes a secondary nitrogen flow line that will create a fluid bed of $N_2$ and $AlO_2$ when sufficient gas flow is allowed to pass through it, thus entraining the $AlO_2$ abrasive within the nitrogen flow, and a handpiece that has a directing nozzle for application of the flow on a specific worksite with a fiber optic bundle including a replaceable light transmissive tip to direct light on the worksite. Although nitrogen is discussed in some of the prior art patents as being suitable for a propellant, in practice it is rarely used.

Accordingly, it is a principal object of the invention to provide a dental implement that can be used with the conventional air powered drill control means already present in the practitioner's office.

It is another object of the invention to provide a dental implement that can be easily attached to utilize the preexisting controls familiar to the operator.

It is a further object of the invention to provide a dental implement that utilizes medical grade nitrogen gas to entrain the abrasive particles, thus lessening the chance of harm in the case of an air embolism and obviating the possibility of contaminants being introduced into the abrasive stream.

Still another object of the invention is to provide a dental implement that uses a diverging valve to pass part of the moving gas into the mixing chamber to agitate the abrasive in a uniform manner consistent with differing gas pressures, thus allowing it to be entrained in the gas.

It is still yet another object of the invention to provide a dental implement that includes a fiber optic bundle with a resilient replaceable light transmissive tip protruding from the handpiece to assist in lighting the work area in the patient's mouth.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
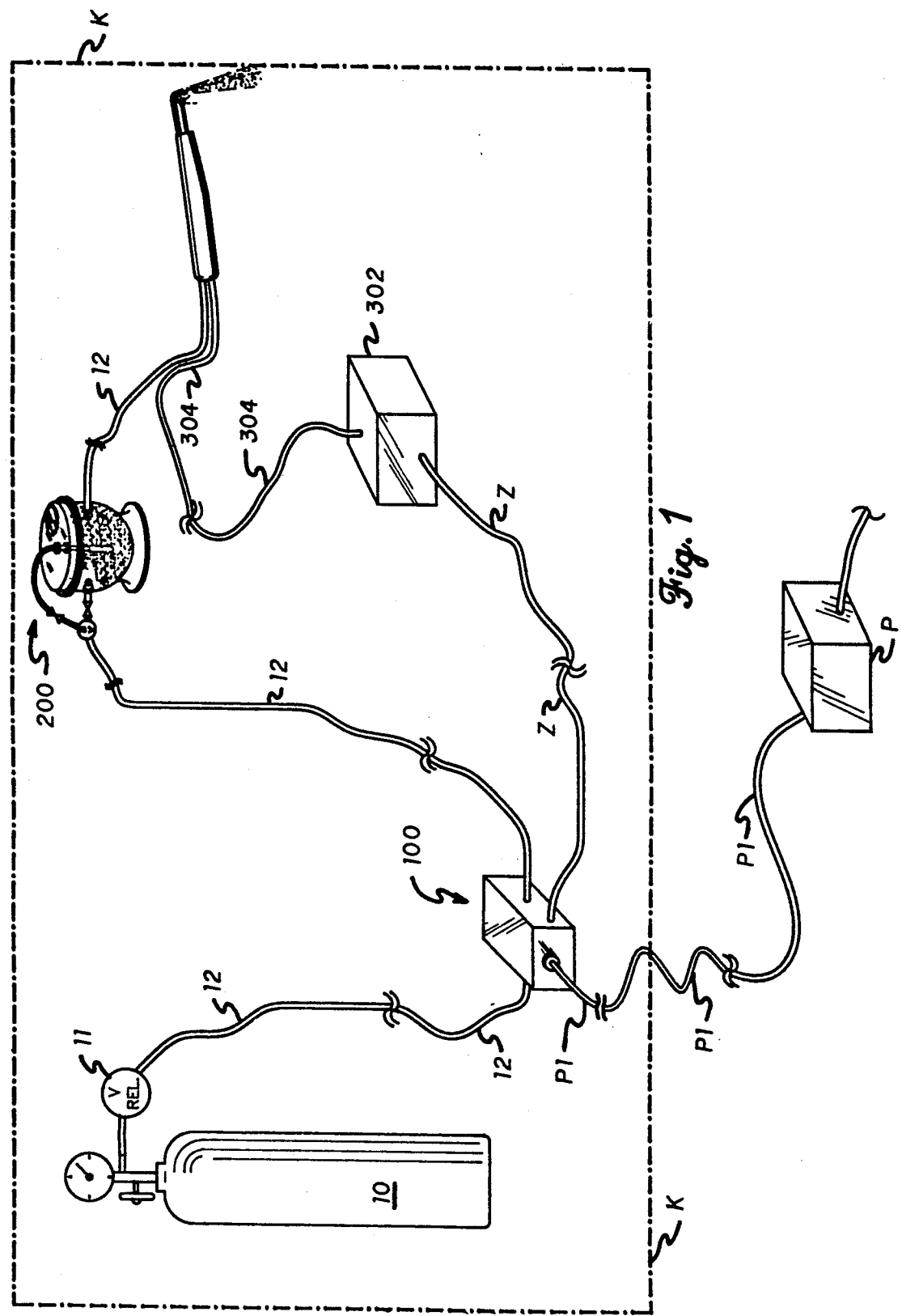
FIG. 1 is a diagrammatic view of the present invention.

Referring to FIG. 1, the present invention is shown. The line K that surrounds the components of the device indicates that in the preferred embodiment, the device in an enclosed single unit, preferably having wheels or the like (not shown). The first component consists of a nitrogen tank 10, containing medical grade nitrogen, that serves as a means to retain the nitrogen under pressure. Preferably, the tank is a size number 20 and includes a conventional regulator, such as a Williams #700 (not shown), to deliver the nitrogen at approximately 150 PSI. Of course other pressures could be chosen, depending on circumstances. Pressures ranging from 110 to 170 PSI are contemplated. Additionally, as is required by law, the gas line would include a safety relief valve 11. The nitrogen then flows through a containing and directing means in the form of a tube 12 that, by virtue of its construction, defines a downstream direction from the tank. The use of the medical grade nitrogen obviates the possibility of contaminants being introduced into the entraining gas stream.

Figure 2:
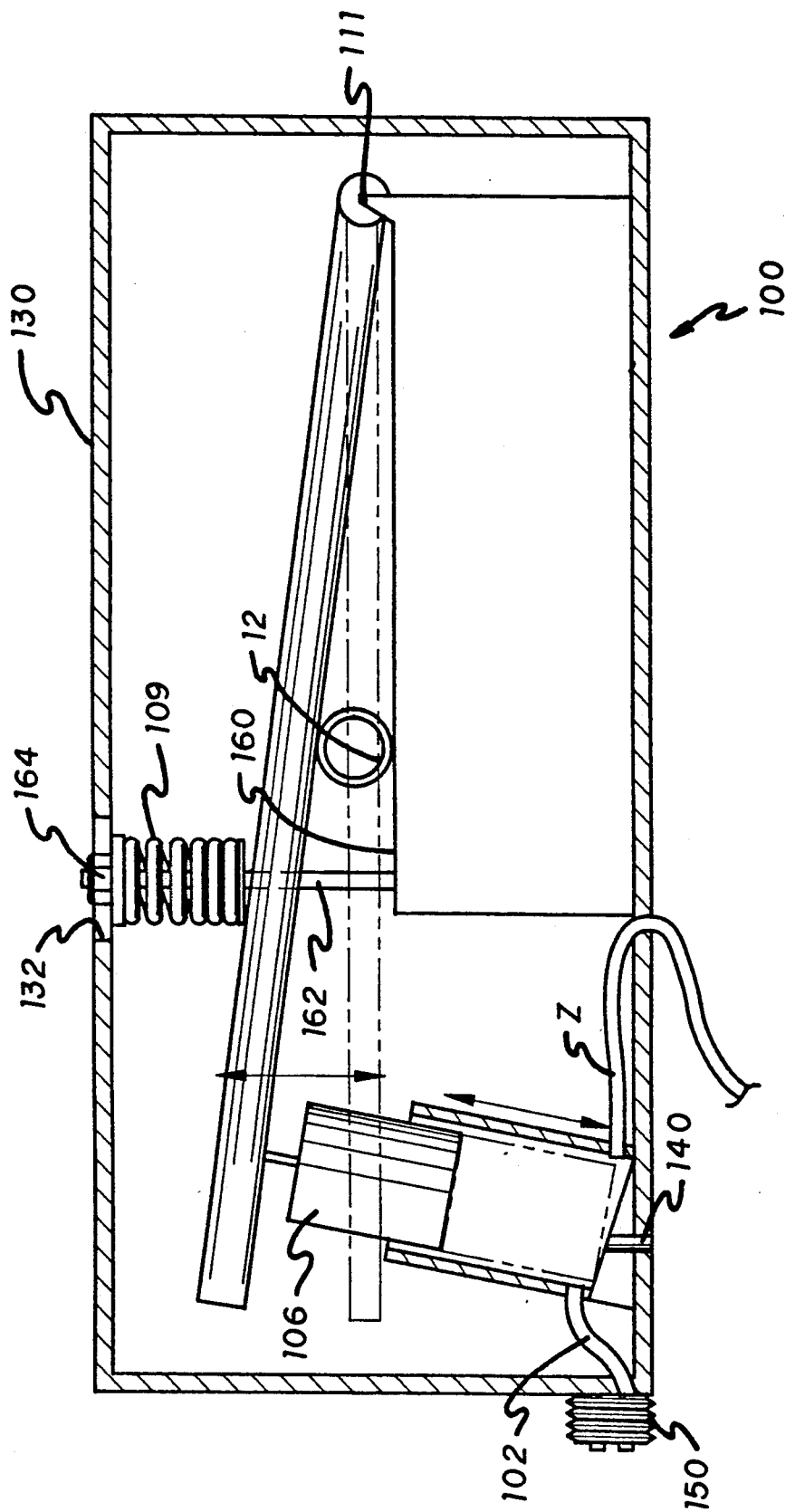
FIG. 2 is a side view of the internal components of the control box.

The nitrogen enters the flow control means 100, best shown in FIG. 2. The control means allows the user to vary the volume of the gas flow upstream from the mixing chamber 200. The flow control means consists of an inlet port 102, a piston chamber 104, a piston 106, typically made of a Teflon material, an adjustable pinch bar biasing spring 109, and a rounded pinch bar 110 that adjustably crimps the tube 12 as it passes through the control means 100. Pinch bar 110 is pivotably attached to the control means 100 at a point 111 and the attachment is configured so as not to overstress the tube 12. The inlet port attaches by means of a conventional four hole connector to the existing air flow control means P that is present in almost all dental offices for attachment to a standard air drill. The airflow control means P delivers air from a compressor or the like (not shown). The user can typically control a flow of compressed air within a range of 0 to 40 PSI, flowing through the tube P1 into inlet port 102. The inlet port 102 has a threaded member 150 that is configured to receive the standard four hole connector on conventional hand piece hoses that are present in most dental offices. This controllable air flows fills the piston chamber 104 with air and forces piston 106 upwards, driving rounded pinch bar 110 upwards about pivot point 111 as shown by arrow 112 in FIG. 2, thus allowing the user to vary the volume of medical grade nitrogen gas allowed to pass through the control means 100 by means of the tube 12. Note that the piston 106 fits loosely into chamber 104 such that when air ceases to flow into the inlet port 102, the piston 106 will almost immediately be forced, by virtue of the pinch bar biasing spring 109, back to the bottom of the chamber 104 and the pinch bar 110 will close off the tube 12 by crimping the tube 12 against the shoulder 160. Additionally, the piston chamber has a vent 140 to enable the air to more quickly exit the chamber 104 once the controllable air flow stops. The vent 140 optionally could have an audible component that would allow the practitioner to determine the volume of nitrogen being passed by the control means. The chamber 104 further includes an air activated switch port Z that directs air entering the chamber 104 into a activation tube Z that leads to the fiber optic housing 302 (see FIG. 1) thus lighting the fiber optic bundle discussed hereinafter. Another feature of the control means 100 is the biasing spring adjustment means. The top wall 130 of the control means 100 has a bore 132 therethrough. This bore 132 is sufficiently large to pass the biasing spring 109 through it to contact the rounded pinch bar 110. Integral with the crimping shoulder 160 is a threaded member 162. The threaded member 162 passes through a pinch bar bore 132 and extends substantially above the top wall 130 of control means 100. The biasing spring 109 is placed on the threaded member 162 and then adjustment nut 164 is engaged with the threaded member 162 such that biasing spring 109 can be adjustably compressed in regards to the pinch bar 110.

Figure 3:
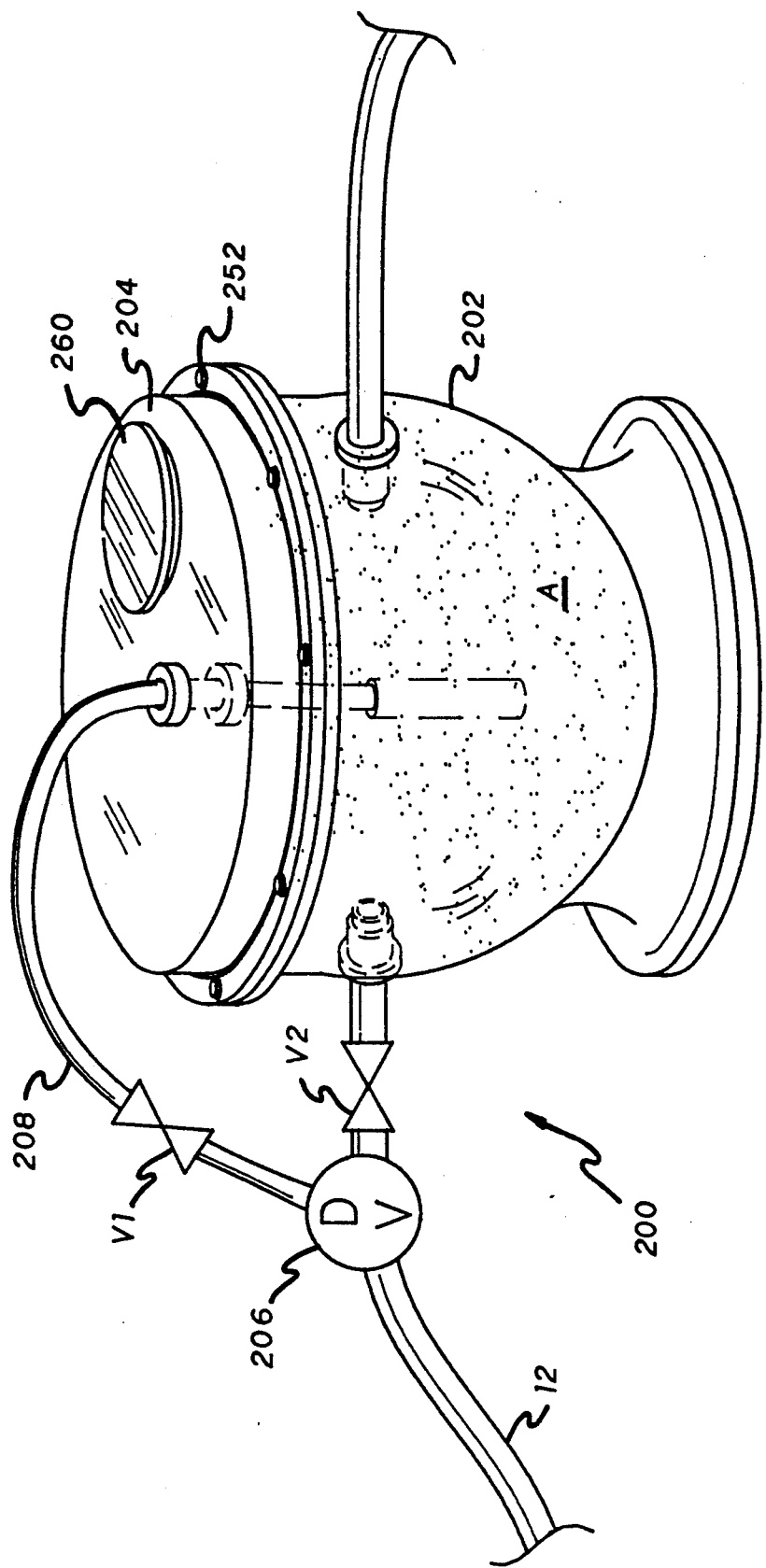
FIG. 3 is a perspective view of the mixing chamber.
Figure 5:
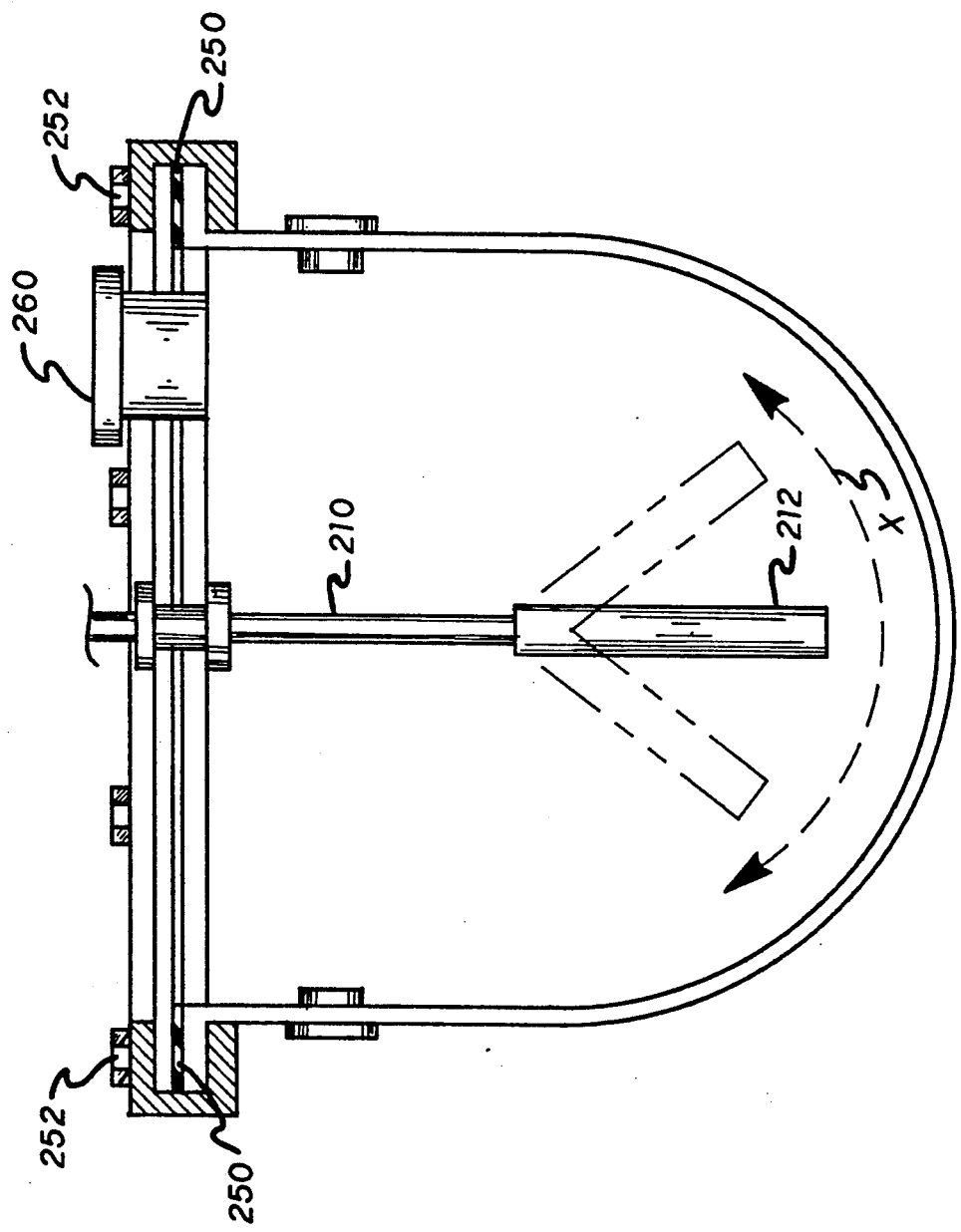
FIG. 5 is a cutaway view of the mixing chamber showing the travel of the flexible tube portion.

Turning to the mixing chamber 200, shown in FIG. 3, it can be seen that it consists of a body portion 202 and top 204. Between the body portion 202 and top 204 is a double O-ring type seal 250 (see FIG. 5) held in place by bolts 252. These bolts are engaged by apertures (not shown) in both the body portion 202 and top 204 of the mixing chamber 200. The number of bolts employed could be as little as two or as many as would be necessary to secure the top 204. Additionally, the top 204 has a threaded fill cap 260 to allow the abrasive A to be replenished when necessary. Both the body portion 202 and top 204 are shown as transparent so that the internal details can be easily seen and the fill level of the abrasive monitored, but it should be understood that one or the other, or both of these pieces could be opaque if desired. Tube 12 carrying the nitrogen gas is split in a "Y" configuration at point 206 that defines a diverting valve. This valve could be either manually adjustable or could be pressure sensitive to the flow of nitrogen. A secondary tube 208 splits away from tube 12 and enters the top 204 of the mixing chamber 200. There are two one-way check valves V1 and V2 present to prevent any backflow from the mixing chamber 200. A rigid portion 210 extends into the mixing chamber 200 and is connected to a flexible end portion 212. Thus, when a sufficient volume of gas is allowed to pass the control unit 100, when it reaches the junction 206, part of the gas is diverted to the secondary tube 208. This then passes through the rigid portion 210 and the flexible portion 212. The flexible portion is free to move about an area, shown as the line X in FIG. 5. This allows for the aluminum oxide abrasive, designated A, to be evenly distributed within the gas stream. The abrasive is preferably about 50 microns in diameter, but different diameters, or mixtures of diameters, could be used. A range of 30 to 60 microns is contemplated. The flexible portion 212 could include a nozzle if necessary, depending on the size if the abrasive particles used. Additionally, under very low gas velocities, the aluminum oxide abrasive will not be agitated and thus the gas stream can be used to clean and/or dry the work area.

Figure 4:
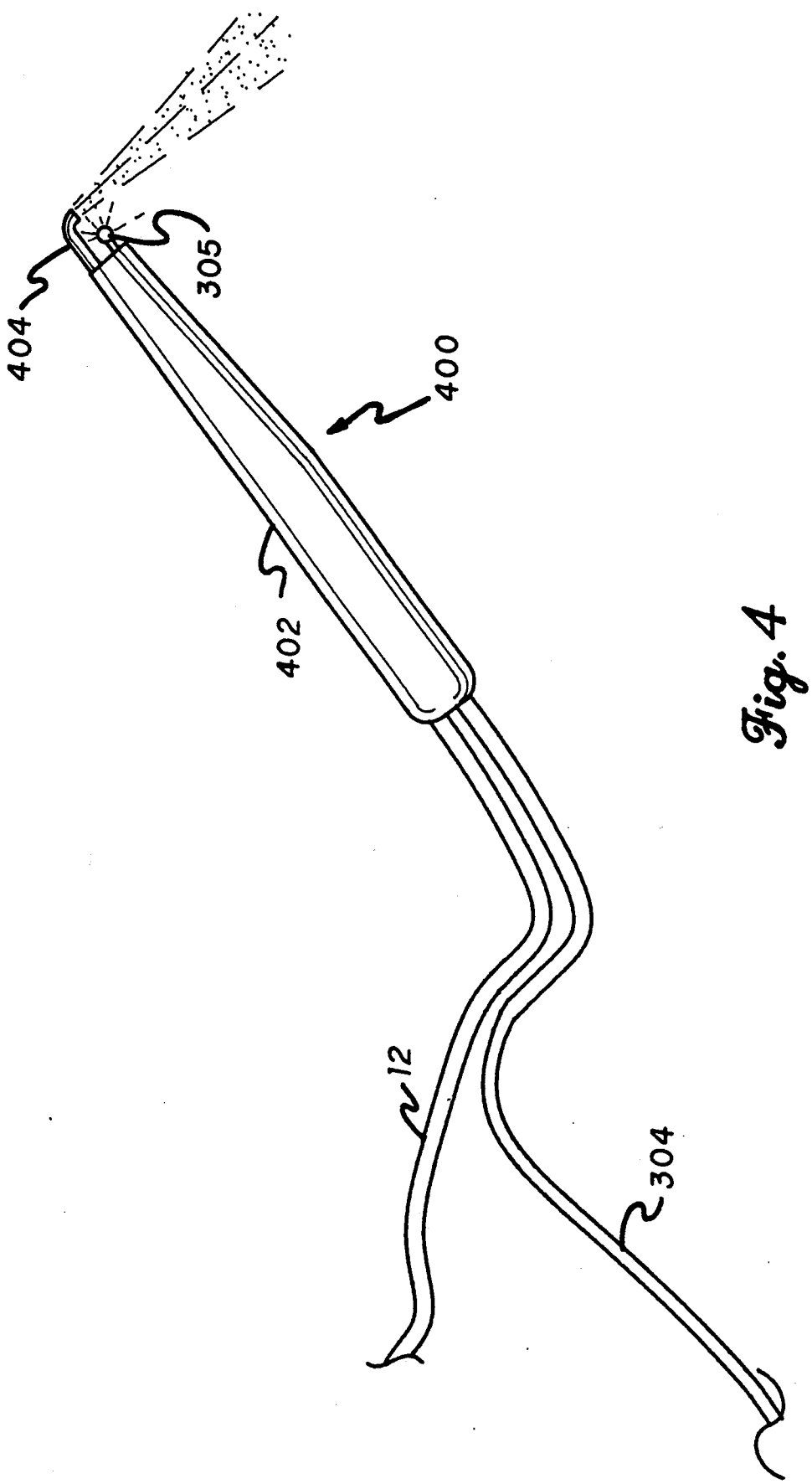
FIG. 4 is a view of the handpiece and fiber optic bundle.

The invention includes a conventional dental light source (not shown) contained within a housing 302. A standard fiber optic bundle 304 transmits the light and projects it into the work area, as seen in FIG. 4. At the end of the fiber optic line is a light projecting tip 305. This tip is made of a semirigid plastic material and is press filled into the handpiece 400. As the light projecting tip becomes abraded by incidental abrasive flow, it can be easily removed and replaced. Preferably, the light is focused approximately 1-4 millimeters away from the end of the nozzle 404. In this type of dentistry, all tactile "feel" is removed, i.e. the pressure feedback from the enamel or decayed material being cut is not present. Thus, good lighting of the work area is critical, since the doctor is operating by visual cues alone. The handpiece 400 has a handle 402, that is adapted to fit easily in the user's hand. The nozzle 404 is made of a sufficiently hard material that it will not be easily worn by the entrained aluminum oxide and, preferably would be removably attached by threading or the like to the handle 402.

It is to be understood that the present invention is not limited to the sole embodiment described above, but encompasses any and all embodiments within the scope of the following claims.

I claim:

1. A dental implement for use with a conventional dentist's airflow control means comprising:
    means to retain medical grade nitrogen under pressure;
    a primary tube means to contain and direct a flow of said nitrogen, said primary tube means defining a nitrogen flow direction downstream of said retaining means;
    control means to vary the volume of said nitrogen flow, said control means being in communication with said retaining means through said tube means, and said control means further including attachment means configured to be engaged with a conventional dentist's airflow control;
    means to entrain granules of aluminum oxide within said nitrogen flow, said entraining means being downstream of said control means and being in communication with said retaining means and said control means through said primary tube means, said entraining means further including a mixing chamber, a mixing chamber top, said mixing chamber containing aluminum oxide granules, a secondary tube means connected to said primary tube means at a first end and connected to said mixing chamber top and extending therethrough at a second end, and a flexible tube portion connected at said second end of said secondary tube means, said flexible portion extending a sufficient distance into said mixing chamber such that said aluminum oxide granules contained therein are agitated when said nitrogen flow passes through said secondary tube means; and
    a handpiece means for directing said flow of nitrogen and said entrained aluminum oxide onto a predetermined location within a patient's oral cavity for the purpose of preparing a tooth for receiving a filling or a composite restoration, said handpiece means including a means for light transmission onto the predetermined area.

2. The dental implement according to claim 1, wherein said means to retain nitrogen under pressure is a tank, said tank including a regulator to deliver nitrogen within the range of 110 to 170 PSI.

3. The dental implement according to claim 1, wherein said control means includes a primary tube means pinch bar having a pivot point, an inlet port that enters a piston chamber, a piston including an integral pinch bar engagement means, and a pinch bar biasing means configured such that said pinch bar is biased to substantially close said primary tube means until compressed air enters said inlet port and said piston chamber thus impelling said piston and said pinch bar engagement means, propelling said pinch bar such that said primary tube means is open for the downstream flow of nitrogen.

4. The dental implement according to claim 1, wherein said aluminum oxide granules are within the range of 30-60 microns in diameter.

5. The dental implement according to claim 1, wherein said means for light transmission is a fiber optic bundle, said fiber optic bundle having a replaceable light transmissive tip.

6. The dental implement according to claim 5, wherein said replaceable light transmissive tip is made of a resilient plastic material and is press-fitted into said handpiece.

7. A dental implement for use with a conventional dentist's airflow control means comprising:

means to retain medical grade nitrogen under pressure;

a primary tube means to contain and direct a flow of said nitrogen, said primary tube means defining a nitrogen flow direction downstream of said retaining means;

control means to vary the volume of said nitrogen flow, said control means being in communication with said retaining means through said tube means, and said control means further including attachment means configured to be engaged with a conventional dentist's airflow control, said control means further including a primary tube means pinch bar having a pivot point, an inlet port that enters a piston chamber, a piston including an integral pinch bar engagement means, and a pinch bar biasing means configured such that said pinch bar is biased to substantially close said primary tube means until compressed air enters said inlet port and said piston chamber thus impelling said piston and said pinch bar engagement means, propelling said pinch bar such that said primary tube means is open for the downstream flow of nitrogen;

means to entrain granules of aluminum oxide within said nitrogen flow, said entraining means being downstream of said control means and being in communication with said retaining means and said control means through said primary tube means, said entraining means further including a mixing chamber, a mixing chamber top, said mixing chamber containing aluminum oxide granules, a secondary tube means connected to said primary tube means at a first end and connected to said mixing chamber top and extending therethrough at a second end, and a flexible tube portion connected at said second end of said secondary tube means, said flexible portion extending a sufficient distance into said mixing chamber such that said aluminum oxide granules contained therein are agitated when said nitrogen flow passes through said secondary tube means; and a handpiece means for directing said flow of nitrogen and said entrained aluminum oxide onto a predetermined location within a patient's oral cavity for the purpose of preparing a tooth for receiving a filling or a composite restoration, said handpiece means including a means for light transmission onto the predetermined area.

8. The dental implement according to claim 7, wherein said means to retain nitrogen under pressure is a tank, said tank including a regulator to deliver nitrogen within a range of 110 to 170 PSI.

9. The dental implement according to claim 7, wherein said aluminum oxide granules are within the range of 30-60 microns in diameter.

10. The dental implement according to claim 7, wherein said means for light transmission is a fiber optic bundle, said fiber optic bundle having a replaceable light transmissive tip.

11. The dental implement according to claim 10, wherein said replaceable light transmissive tip is made of a resilient plastic material and is press-fitted into said handpiece.

* * * * *